(12) United States Patent
Freedman et al.

(10) Patent No.: US 9,745,101 B2
(45) Date of Patent: Aug. 29, 2017

(54) CONTAINER WITH INSERT

(71) Applicant: CSP TECHNOLOGIES, INC., Norristown, PA (US)

(72) Inventors: Jonathan R. Freedman, Auburn, AL (US); William S. Abrams, Auburn, AL (US); John Belfance, Phenix City, AL (US)

(73) Assignee: CSP TECHNOLOGIES, INC., Auburn, IL (US)

( * ) Notice: Subject to any disclaimer, the term of this patent is extended or adjusted under 35 U.S.C. 154(b) by 0 days.

(21) Appl. No.: 14/357,291

(22) PCT Filed: Nov. 7, 2012

(86) PCT No.: PCT/US2012/063803
§ 371 (c)(1),
(2) Date: May 9, 2014

(87) PCT Pub. No.: WO2013/070664
PCT Pub. Date: May 16, 2013

(65) Prior Publication Data
US 2014/0319149 A1  Oct. 30, 2014

Related U.S. Application Data

(60) Provisional application No. 61/610,688, filed on Mar. 14, 2012, provisional application No. 61/585,367, (Continued)

(51) Int. Cl.
*B65D 25/04* (2006.01)
*B65D 25/10* (2006.01)
(Continued)

(52) U.S. Cl.
CPC .............. *B65D 25/04* (2013.01); *B65D 25/10* (2013.01); *B65D 43/162* (2013.01);
(Continued)

(58) Field of Classification Search
CPC ............ B65D 2209/00; B65D 83/0888; B65D 25/10; B65D 25/04
(Continued)

(56) References Cited

U.S. PATENT DOCUMENTS 4,789,059 A * 12/1988 Kim .............................. 206/246
5,027,972 A *  7/1991 Bartholomew ............... 220/526
(Continued)

FOREIGN PATENT DOCUMENTS

| EP | 0892673 B1 | 2/2004 |
|---|---|---|
| JP | 2003-118781 A | 4/2003 |
| JP | 2003-146381 A | 5/2003 |
| KR | 20-0389372 | 7/2005 |
| WO | WO2007/065162 A2 | 6/2007 |

*Primary Examiner* — Jeffrey Allen
*Assistant Examiner* — Jennifer Castriotta
(74) *Attorney, Agent, or Firm* — David B. Gornish; Eckert Seamans Cherin & Mellott, LLC

(57) ABSTRACT

A vial and insert assembly includes a vial having an interior and an opening leading to the interior. The assembly further includes an insert configured to fit within the interior. The insert includes a first receptacle for housing a plurality of unused products and a second receptacle for housing a plurality of used products.

12 Claims, 5 Drawing Sheets

Related U.S. Application Data filed on Jan. 11, 2012, provisional application No. 61/557,642, filed on Nov. 9, 2011.

(51) Int. Cl.
   *B65D 83/08* (2006.01)
   *G01N 33/487* (2006.01)
   *B65D 81/26* (2006.01)
   *B65D 43/16* (2006.01)

(52) U.S. Cl.
   CPC ....... *B65D 81/267* (2013.01); *B65D 83/0888* (2013.01); *G01N 33/48778* (2013.01); *B65D 2209/00* (2013.01); *B65D 2543/00083* (2013.01); *B65D 2543/00296* (2013.01); *B65D 2543/00527* (2013.01); *B65D 2543/00537* (2013.01); *B65D 2543/00842* (2013.01)

(58) Field of Classification Search
   USPC ...... 221/102, 97, 34; 220/23.86, 23.87, 528, 220/505, 527, 908; 206/223
   See application file for complete search history.

(56) References Cited

U.S. PATENT DOCUMENTS

| | | |
|---|---|---|
| 5,551,591 A * | 9/1996 | Laib .............................. 220/528 |
| 6,303,064 B1 | 10/2001 | Abrams et al. |
| RE37,676 E | 4/2002 | Abrams et al. |
| 6,769,558 B1 | 8/2004 | Bucholtz |
| 7,213,720 B2 | 5/2007 | Giraud |
| 7,413,083 B2 | 8/2008 | Belfance et al. |
| 7,950,546 B2 | 5/2011 | Giraud et al. |
| 8,302,810 B2 * | 11/2012 | Mulhem et al. ................ 221/34 |
| 2003/0173237 A1 * | 9/2003 | Kim .............................. 206/217 |
| 2006/0219585 A1 | 10/2006 | Cho |
| 2007/0196242 A1 * | 8/2007 | Boozer ............. G01N 33/4875 422/400 |
| 2009/0026209 A1 * | 1/2009 | Huntington et al. .......... 220/500 |
| 2009/0206086 A1 * | 8/2009 | Gwee ............................ 220/503 |
| 2011/0123416 A1 | 5/2011 | Giraud et al. |
| 2011/0127269 A1 | 6/2011 | Bucholtz et al. |
| 2012/0080330 A1 * | 4/2012 | Rush et al. .................... 206/305 |

* cited by examiner

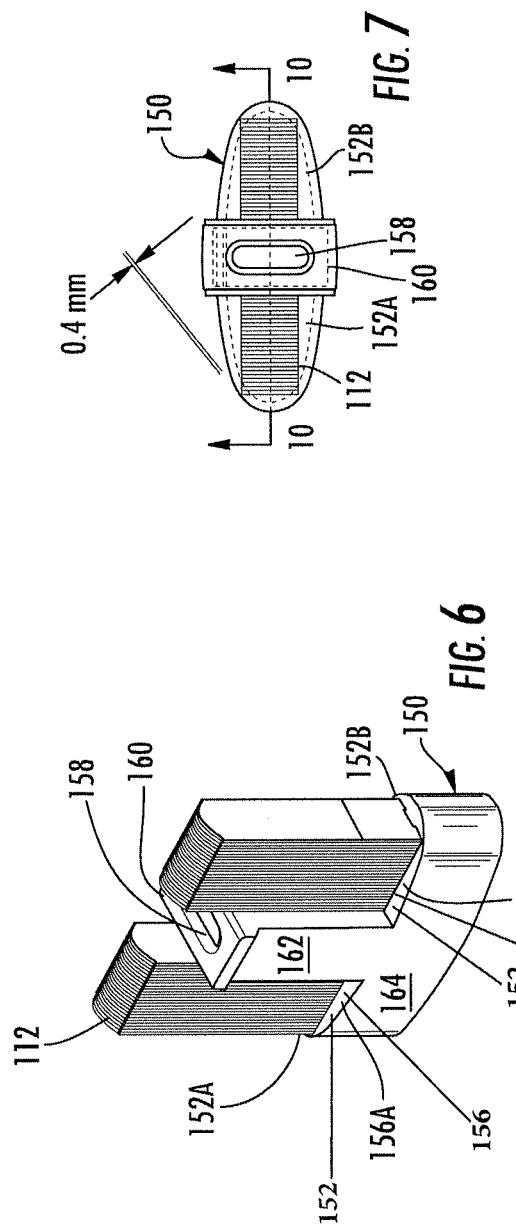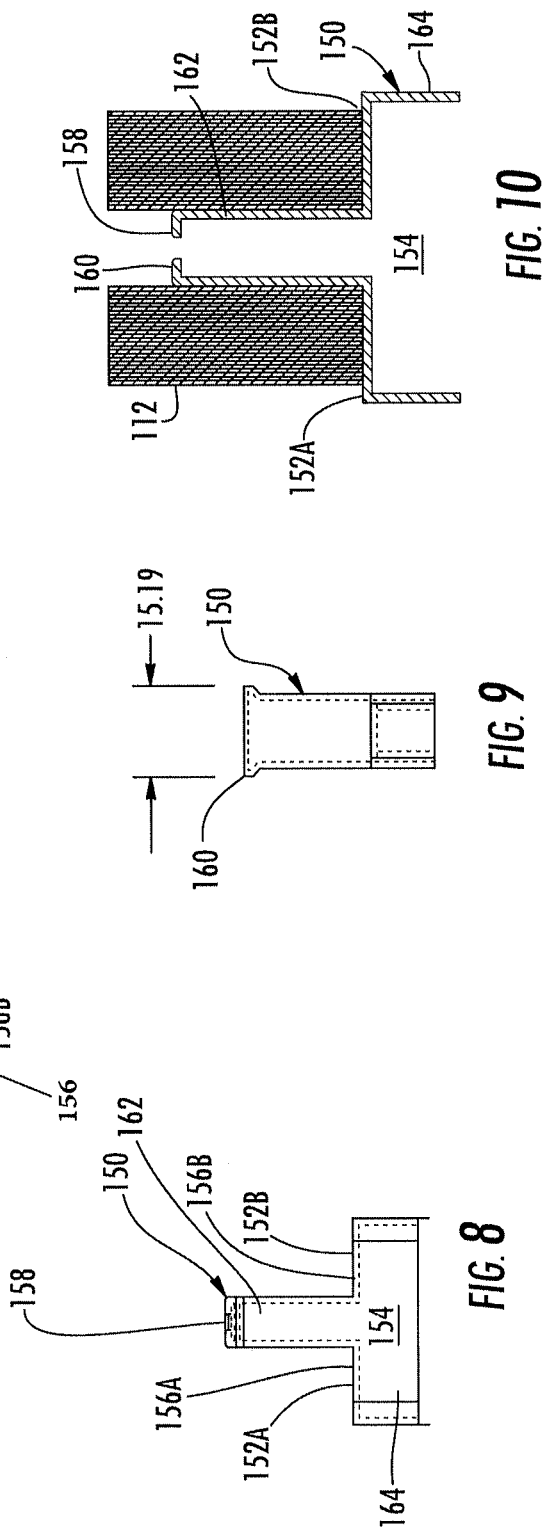

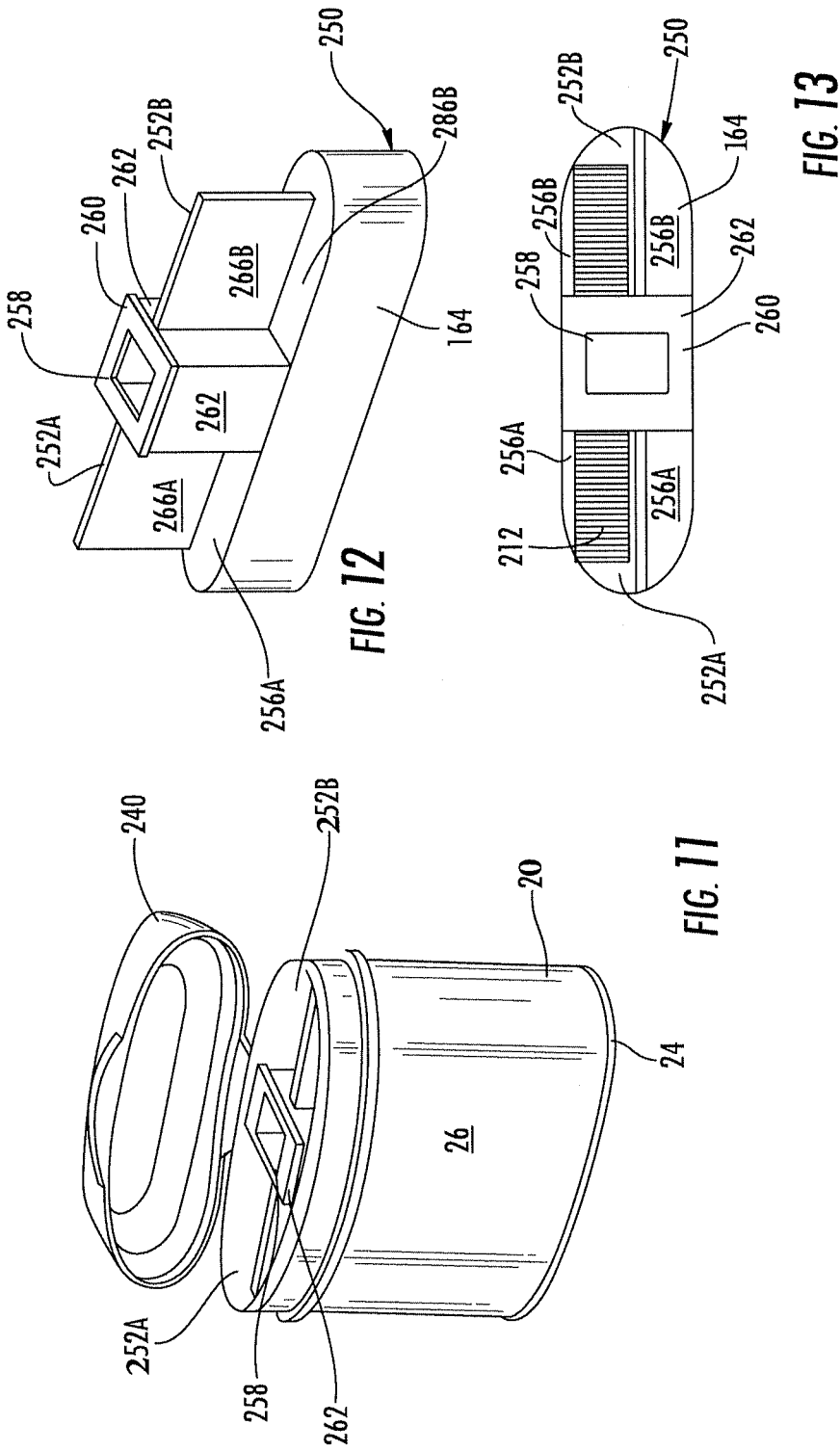

CONTAINER WITH INSERT

CROSS REFERENCE TO RELATED APPLICATIONS

This application is a U.S. National Phase Application of International Application No. PCT/US2012/063803, filed Nov. 7, 2012 which claims priority from U.S. Provisional Application Ser. No. 61/610,688, filed Mar. 14, 2012; 61/585,367, filed Jan. 11, 2012; and 61/557,642, filed Nov. 9, 2011.

FIELD OF INVENTION

The present invention relates to a vial and insert assembly including a vial having an interior and an opening leading to the interior. The assembly further includes an insert configured to fit within the interior. The insert includes a first receptacle for housing a plurality of unused products and a second receptacle for housing a plurality of used products.

BACKGROUND OF THE INVENTION

Product containers used for consumer products are typically configured for the packaging and dispensing of new, unused product. Accordingly, after a product that has been removed from the container is used, the consumer typically needs to find a location to dispense of the used product. However, proper dispensing receptacles are not always readily available. Additionally, not all types of used consumer products are dispensed in the same manner, or in the same types of receptacles. Indeed, in some instances, it may be undesirable to dispose of a used product in an exposed manner in a waste receptacle with other types of waste or disposable materials.

BRIEF SUMMARY OF THE INVENTION

Embodiments of the present invention relate to product containers or dispensers for use with a variety of consumer products or pharmaceutical products and supplies, such as, for example, glucose strips, among other products. Moreover, the present invention relates to product containers dispensers that are configured to allow for both the storage of new or unused consumer product and an area for at least the temporary disposal of that product after the product has been used. Additionally, according to certain embodiments, the product container may include seals that assist in controlling the ingress and/or egress of moisture into/out of an interior space of the product dispenser, and thereby may assist in controlling the conditions in an interior space of the container.

According to certain embodiments, a vial and insert assembly is provided that includes a vial having an interior and an opening leading to the interior. The assembly also includes an insert that is configured to fit within the interior. The insert has a first receptacle for housing a plurality of unused products and a second receptacle for housing a plurality of used products.

According to another embodiment, a vial and insert assembly is provided that includes a vial having an interior and an opening leading to the interior. The insert is configured to fit within the interior. The insert includes a first receptacle for housing a plurality of unused products and a second receptacle for housing a plurality of used products. The second receptacle is defined by an interior region of the insert. At least a portion of the second receptacle extends beneath the first receptacle.

According to another embodiment, a vial and insert assembly is provided that includes a vial having an interior and an opening leading to the interior. The insert is configured to fit within the interior. The insert also includes a first receptacle for housing a plurality of unused products and a second receptacle for housing a plurality of used products. Additionally, the insert has an exterior surface, at least a portion of the exterior surface configured to elevate the unused products housed within the first receptacle. Further the second receptacle is defined by an interior region of the insert. The insert further includes a rib located within the first receptacle for aligning the plurality of unused products positioned within the first receptacle.

BRIEF DESCRIPTION OF SEVERAL VIEWS OF THE DRAWINGS

FIG. 6 is a front perspective view of another embodiment of an insert in accordance with the invention.

FIG. 7 is a top plan view of the insert of FIG. 6.

FIG. 8 is front elevation of the insert of FIG. 6.

FIG. 9 is a right side elevation of the insert of FIG. 6.

FIG. 10 is a cross section taken along line 10-10 of FIG. 7.

FIG. 11 is a front perspective view of a vial with another embodiment of an insert in accordance with the invention.

FIG. 12 is a front perspective view of the insert of FIG. 11.

FIG. 13 is a top plan view of the vial and insert assembly of FIG. 11.

DETAILED DESCRIPTION OF THE EXEMPLARY EMBODIMENTS

Figure 1:
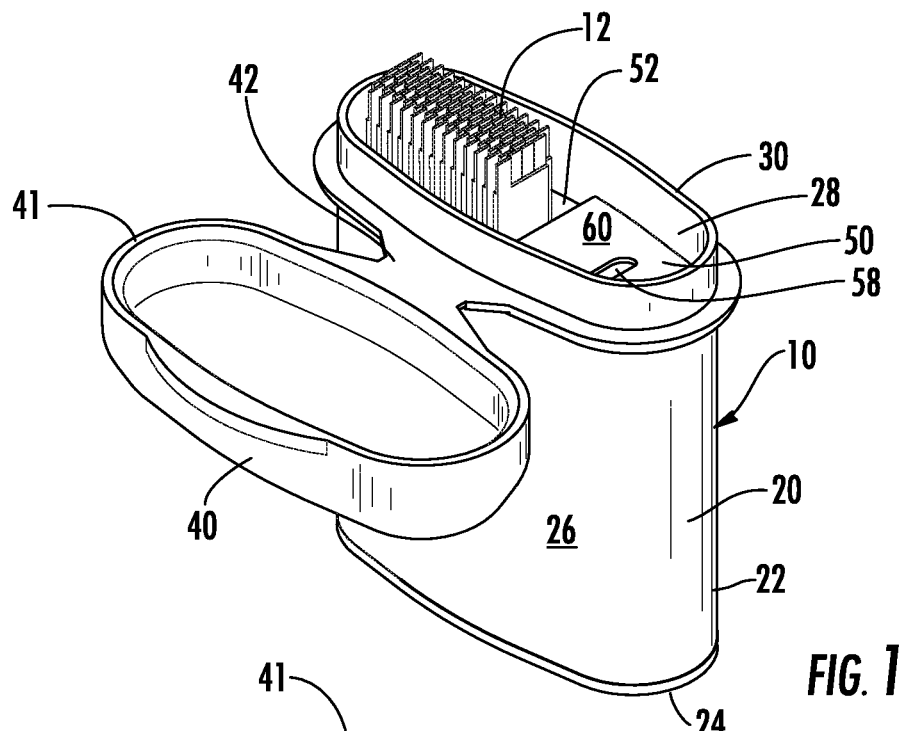
FIG. 1 is a rear perspective view of a vial with insert in accordance with an illustrated embodiment of the invention.
Figure 2:
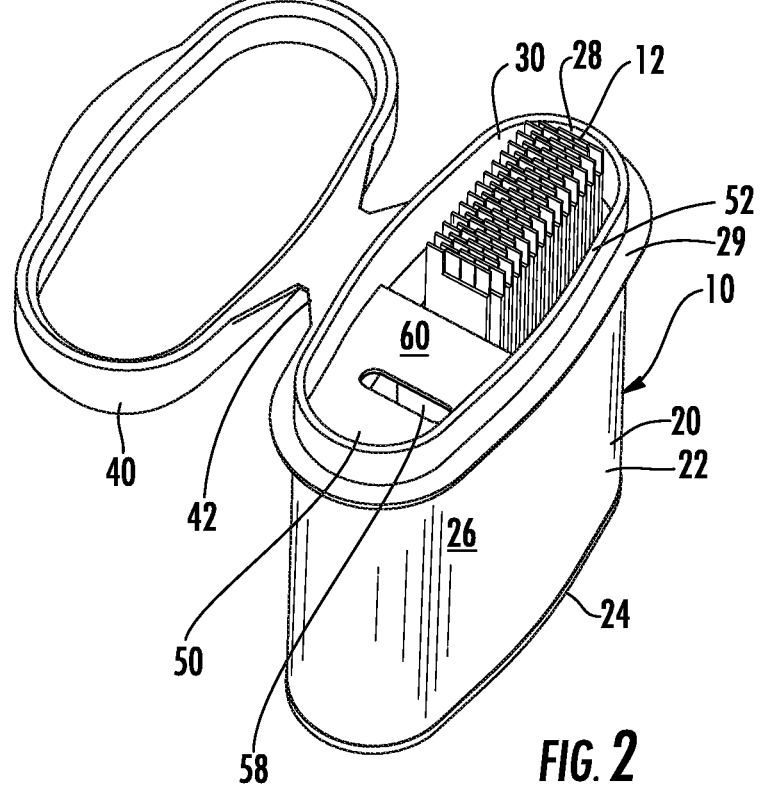
FIG. 2 is a front perspective view of the vial with insert shown in FIG. 1.
Figure 3:
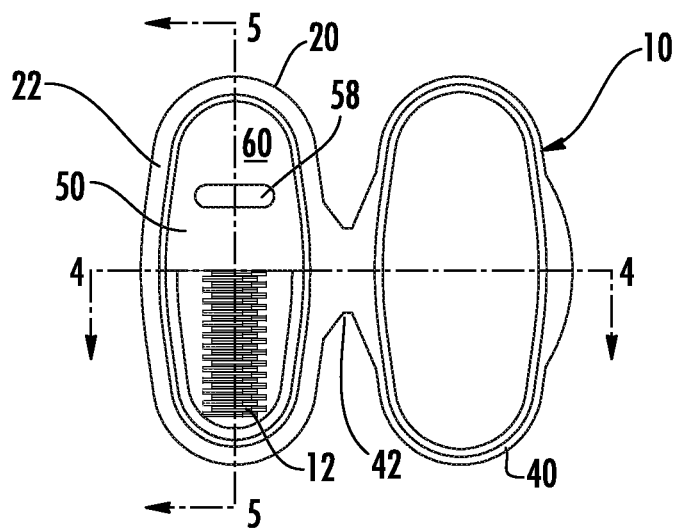
FIG. 3 is a top plan view of the vial with insert shown in FIG. 1.

The present invention will now be described more fully with reference to the accompanying drawings, in which several embodiments are shown. This invention may, however, be embodied in many different forms and should not be construed as limited to the embodiments set forth here. Rather, these embodiments are examples of the invention, which has the full scope indicated by the language of the claims. Like numbers refer to like elements throughout.

A first embodiment of a vial and insert assembly 10 is shown in FIGS. 1-5. As shown, the vial and insert assembly 10 includes a vial 20 and an insert 50. The insert 50 fits within an interior 28 of the vial 20 and includes a first receptacle 52 for elevating and/or placement of a plurality of new products 12 that are to be stored within the vial 20, and a second receptacle 54 for housing a plurality of used products 12. Moreover, new products 12 removed from the first receptacle 52 may subsequently, such as after being used, be disposed of and/or retained in the second receptacle 54.

The vial 20 includes a body 22 having a base 24 and side wall 26 depending upwardly therefrom. The base 24 and side wall 26 together define an interior 28 of the body 22. An upper edge of side wall 26 may define an opening 30 that leads and/or provides access to the interior 28. In the embodiment shown, the side wall 26 is tubular and has a generally oval cross-sectional shape. However, it should be understood that the side wall 26 can take on a variety of other shapes as well. The vial 20 could take on a variety of other configurations from that disclosed above. Examples of vial 20 configurations include, but are not limited to, any of the configurations disclosed in U.S. Pat. Nos. 6,769,558, RE 37,676, 6,303,064, 7,213,720, and 7,950,546, U.S. Pat. Pub. No. 2011/0123416, or WO 2007/065162, each of which is incorporated herein by reference as if fully set forth.

The vial 20 further includes a cap 40 that, when the vial 20 is in a closed position, is removably affixed over the opening 30. The vial 20 may be moved into an open position, as shown in FIGS. 1-5 by moving the cap 40 away from the opening 30, such as moving the cap 40 so that the cap 40 is not covering the opening 30, as shown, for example, in FIGS. 1-5.

In the embodiment illustrated in FIGS. 1-5, the cap 40 is connected to the body 22 by a hinge 42. However, according to other embodiments, the cap 40 may be completely removable from the body 22, such as being a separate, removable component that is not attached to the vial 20. A variety of different types of hinges 42 may be employed to operably attach the cap 40 to the vial body 22. For example, according to certain embodiments, the hinge 42 may be a "living hinge," such that the vial body 22 and cap 40 are formed integrally and connected by a section of material sufficiently thin so to be foldable and therefore allow for pivoting therebetween. According to other embodiments, the hinge 42 may be a separate mechanical element that connects the body 22 and cap 40 and permits pivoting therebetween.

Figure 4:
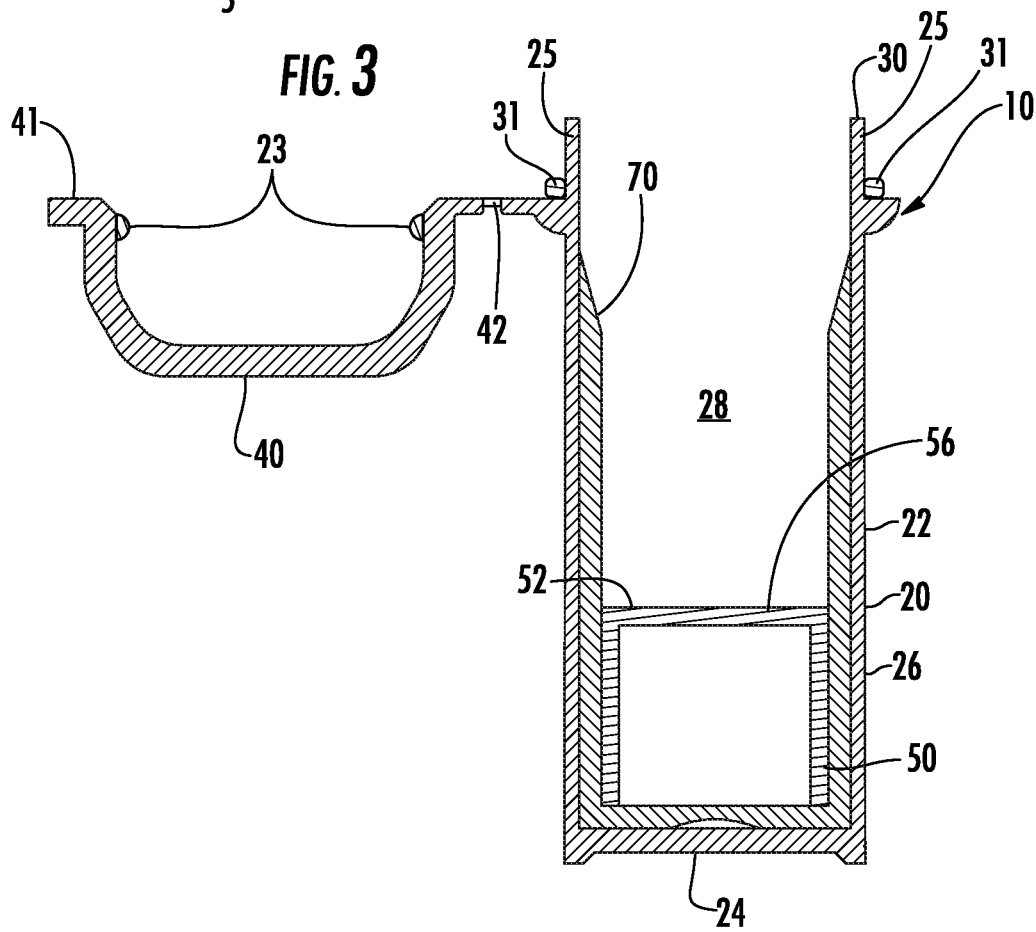
FIG. 4 is a cross section taken along line 4-4 of FIG. 3.

According to certain embodiments, the vial 20 and cap 40 are configured for engagement with each other to form a moisture-tight seal when in the closed position. For example, an upper lip portion 25 of the sidewall 26 may be positioned and sized such that the upper lip portion 25 is engaged by the cap 40 when the cap 40 is placed into to the closed position. According to certain embodiments, when engaged by the cap 40, the upper lip portion 25 may deform, bend, and/or deflect so as to create a relatively secure engagement between the upper lip portion 25 and cap 40 that provides a seal that prevents or minimizes moisture outside of the vial and insert assembly 10 from entering into the interior 28 through the opening 30. Alternatively, according to other embodiments, at least portions of the cap 40 that engage the upper lip portion 25 when the cap 40 is in the closed position may be configured to deform, bend, and/or deflect in a manner that allows for the formation of a seal between the cap 40 and the vial 20. Alternatively, according to other embodiments, the vial body 22 and/or cap 40 may be operably connected to an upper seal 23, such as, for example, as shown in FIG. 4, an elastomeric seal, that is configured to deform and/or press against the adjacent cap 40 and/or body 22 when the cap 40 is in a closed position so as to form the seal that prevents or minimizes the entry of moisture into the interior 28.

Additionally, the vial body 22 may include a shoulder 29 which a lower portion 41 of the cap 40 may abut against when the cap 40 is in the closed position. According to certain embodiments, the shoulder 29 may provide a stop that limits the portion or amount of the sidewall 26 that the cap 40 may abut against and/or be secured to when the cap 40 is in the closed position. Such a stop may be intended to prevent the cap 40 from becoming undesirably difficult to move from the closed to open position due any forces created by the engagement between the cap 40 and the sidewall 26 and/or any seal formed there between. Additionally, as shown in FIG. 4, according to certain embodiments, a lower seal 31, such as an elastomeric seal, may be placed on the lower portion 41 and/or shoulder 29 so as to provide a seal between the lower portion 41 and shoulder 29 when the cap 40 is in a closed position that prevents the ingress of moisture from the environment outside of the vial and insert assembly 10 into the interior 28.

According to certain embodiments, the vial body 22 and cap 40 may be made from, for example, polyethylene or polypropylene, among other materials. Additionally, according to certain embodiments, the vial 20 includes a desiccant plastic material, such as a desiccant plastic liner 70. For example, according to certain embodiments, the desiccant liner 70 may line at least a portion of the inner surface 27 of the sidewall 26, as shown, for example, in FIGS. 4 and 5. The desiccant plastic material may be, for example, of the type disclosed in EP 0892673, which is incorporated herein by reference as if fully set forth.

The assembly 10 further includes an insert 50. As shown in FIGS. 1-5, the insert 50 is positioned within the interior 28 of the vial 20. According to certain embodiments, the insert 50 is of a similar shape and/or size of at least a portion of the interior 28 of the vial body 22. Moreover, at least a portion of the outer surface(s) 60 of the insert 50 is configured to generally match and/or mate the shape of at least a portion of the interior 28 and/or at least a portion of the desiccant liner 70. Such a configuration of the insert 50 may allow the insert 50 to securely fit within the interior 28 of the vial body 22. For example, according to certain embodiments, the vial 20 and/or insert 50 may be configured to allow the insert 50 to be secured in the interior 28 of the vial 20 by a press or snap fit.

Additionally, similarities between the size and/or shape of the insert 50 and the interior 28 and/or desiccant liner 70 may allow the insert 50 to serve as a reinforcing member that prevents undesirable deformation of at least a portion of the side wall 26 of the vial body 22. For example, the insert 50 may provide reinforcement to prevent portions of the side wall 26 from deforming while the cap 40 is being moved to the closed position about the opening 30, while also allowing those portions of the sidewall 26, if any, that are intended to be deformed for purposes of forming the above-discussed seal. Additionally, such reinforcement may enhance the ability to obtain and/or retain a seal formed between the vial 20 and cap 40 when the cap 40 is in the closed position, as disclosed in U.S. Patent Pub. No. 2011/0127269, which is incorporated herein by reference as if fully set forth.

Figure 5:
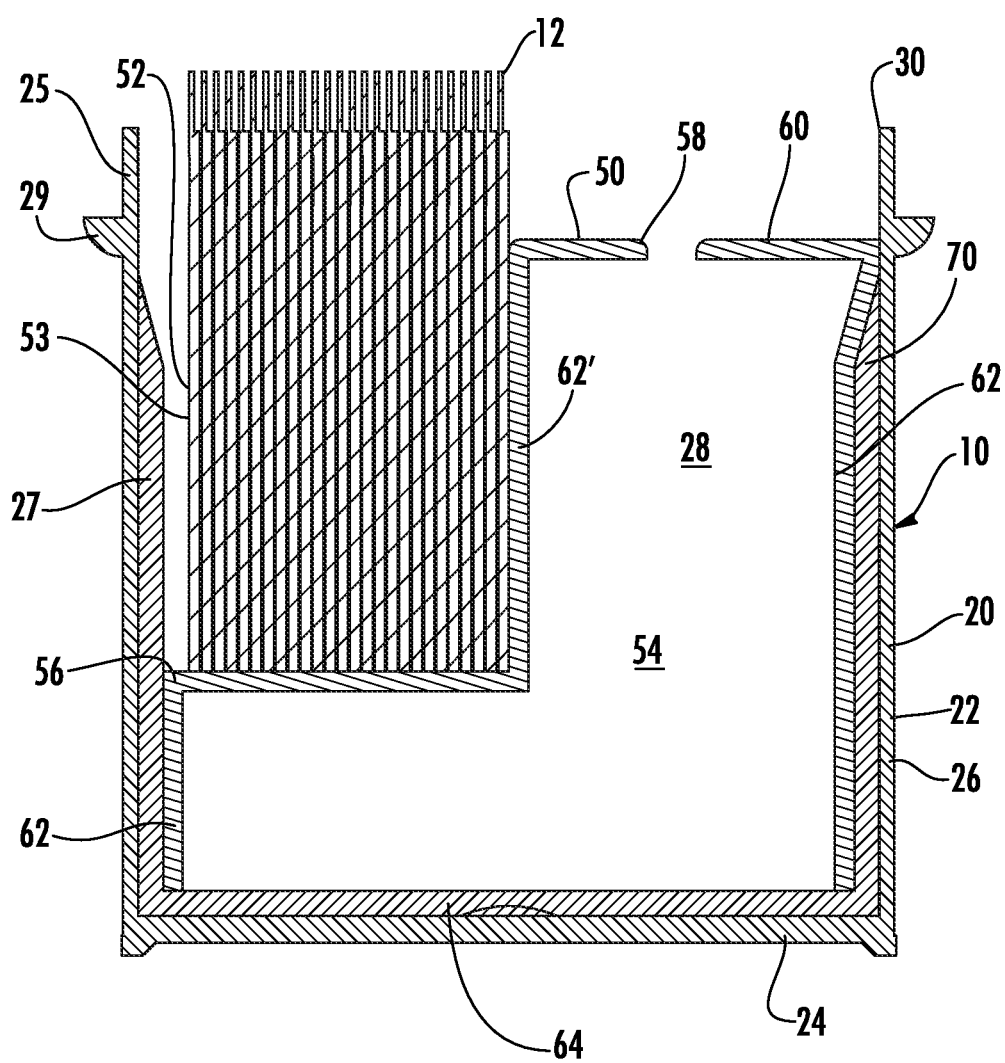
FIG. 5 is a cross section taken along line 5-5 of FIG. 4.

As best shown in FIG. 5, the insert 50 includes a first receptacle 52 for housing a plurality of new products 12 and a second receptacle 54 for housing a plurality of used products 12. In the illustrated embodiment, the products 12 are in the form of elongate strips, such as diagnostic test strips, for example blood glucose test strips. However, a variety of other types of products, including products having different shapes and/or configurations than the products 12 illustrated in FIG. 5, could be contained within the assembly 10.

Referring still to FIG. 5, the first receptacle 52 is defined, at least in part, by an elevating surface 56 of the insert 50. As shown, according to certain embodiments, the first receptacle 52 may be an interior region 53 that is formed in the insert 50 and/or along a top portion of the insert 50. In the embodiment illustrated in FIG. 5, new or unused products 12 sit on the elevating surface 56 of the insert 50 that is position within or below the interior region 53. The elevating surface 56 elevates the new or unused products 12 so those products 12 can be readily accessed by a user and removed from the assembly 10.

According to certain embodiments, the second receptacle 54 is defined by an interior region 53 of the insert 50. For example, according to certain embodiments, the interior region 53 may be at least partially positioned within the interior 28 of the vial body 22 beneath an outer surface 60 of the insert 50. According to certain embodiments, the interior region 53 may also be defined by a vertical portion 62 of the insert 50 that is positioned against and/or adjacent to the desiccant liner 70 or side wall 26 of the vial body 22. Further, as shown in at least FIG. 5, according to certain embodiments, the bottom portion of the interior region 53 may be defined by the bottom wall 64 of the vial body 22 and/or desiccant liner 70. Alternatively, the insert 50 may include a lower wall that extends at the bottom of the vertical portion 62.

The insert 50 includes an opening 58 that is formed in the outer surface 60 of the vial 50 and which is in communication with the interior region 53. In the illustrated embodiment, the opening 58 is formed in an uppermost surface 60 of the insert 50, formed atop the vertical portion 62 of the insert 50, so as to be easily accessible to a user of the assembly 10. The opening 58 in the embodiment shown is in the form of a slot, which is sized and shaped to accept the strips 12 housed in this embodiment of the assembly. In other embodiments the opening 58 could take on other shapes to accept products 12 having other shapes.

In the illustrated embodiment, the insert 50 has a substantially "L" shape, which may be formed by inwardly offsetting a portion of the vertical portion 62' away from other portions of the vertical portion 62 that are adjacent to the side wall 26 (and associated desiccant liner 70) of the vial body 22. Moreover, such offset may be provided by the extension of the elevating surface 56 away from the side wall 26 of the vial body 22 and toward an inner portion of the interior 28 of the vial body 22. As shown in FIG. 5, the elevating surface 56 is also located at a position in the interior 28 that is lower than the position of the upper most surface 60. Additionally, a horizontal portion 64 of the vial body 22 and/or desiccant liner 70 extends beneath both the uppermost surface 60 and the elevating surface 56 of the insert 50 in a horizontal direction.

In use, the products 12 are supplied in the first receptacle 52 with the assembly 10 in the closed position. The products 12 are elevated by the elevating surface 56 of the first receptacle, as shown in FIG. 5, to be easily reached by a user. The user may move the cap 40 into the opened position, as shown in FIGS. 1-5 and remove one or more products 12 from the first receptacle 52. The user can then use any retrieved products 12 and then dispose of the used products 12 by inserting them into opening 58 and into the second receptacle 54. According to certain embodiments, when all products 12 from the first receptacle 52 have been used and placed into the second receptacle 54 the user can reclose and dispose of the entire assembly 10. According to other embodiments, the assembly 10 may be opened and closed over a period of time as new or unused products 12 are used by the user. Further, according to certain embodiments, the insert 50 may be removable from the vial body 22 such that the second receptacle 54 may be at least periodically be emptied of used products 12.

The insert 50 may be formed from a variety of different materials, including, for example, polyethylene or polypropylene, among other materials. According to certain embodiments, the insert 50 may be formed of a desiccant plastic material, such as that disclosed in EP 0892673.

Another illustrated embodiment of an insert 150 is shown in FIGS. 6-10. The insert 150 of this illustrated embodiment is also adaptable for use with a number of different vial configurations, such as, for example, the vial 20 shown in FIGS. 1-5.

The insert 150 of FIGS. 6-10 differs from that shown in FIGS. 1-5 in that it takes on a substantially inverted "T" shape, rather than the "L" shape of the insert 50 shown in FIGS. 1-5. Accordingly, the vertical portion 162 extends upward from a substantially central location along the length of the horizontal portion 164. This results in the first receptacle 152 being divided into first and second portions 152A, 152B, and elevating surface 156 being divided into first and second portions 156A, 156B. As shown, the unused products 112 are divided into two portions that are housed in the first and second portions 152A, 152B of the first receptacle 152. While FIGS. 6-10 illustrate the vertical portion 162 at a substantially central location along the length of the horizontal portion 164, vertical portion 162 may be positioned at a variety of different locations along the horizontal portion 164. Additionally, the first and second portions 156A, 156B may or may not have similar sizes and/or shapes. As shown, FIGS. 7-9 provide some exemplary dimensions for the insert 150.

As shown, the new or unused products 112 may be housed in the first and/or second portions 152A, 152B of the first receptacle 152. After use, products 112 may subsequently be inserted through an opening 158 in the uppermost surface 160 of the insert 150 and into the second receptacle 154.

Another exemplary embodiment of an insert 250 is illustrated in FIGS. 11-13. The insert 250 illustrated in FIGS. 11-13 differs from the insert 150 shown in FIGS. 6-10 in that the insert 250 includes two ribs 266A, 266B. As illustrated, the ribs 266A, 266B extend vertically upwards from elevating surfaces 256A, 256B and extend across from the vertical portion 262 to opposite sides of vial 20 in a direction that is substantially parallel with the longitudinally extending portion of vial side wall 22.

As shown in FIG. 13, new or unused products 212 may be stored behind the ribs 266A, 266B, between the ribs 266A, 266B and the rear portion of vial side wall. Ribs 266A, 266B thus function to align unused products 212 stored in the first receptacles 252A, 252B, and to protect products from contact with vial lid 240, which could occur for example during closing of the vial 20 and potentially damage products. After use, used products 212 may subsequently be inserted through an opening 258 in the uppermost surface 260 of the insert 250 and into the second receptacle 154.

While the vial 20 and inserts 50, 150, 250 have been illustrated in particular shapes and configurations, the vials and inserts 50, 150, 250 can take on a variety of other, different sizes and shapes.

What is claimed is:

1. A vial and insert assembly, comprising:
   a vial having an interior and an opening leading to the interior; and
   an insert configured to fit within the interior, the insert having a first receptacle for housing a plurality of unused elongate strips and a second receptacle for housing a plurality of used elongate strips, said unused and used elongate strips having a width and a thickness, the second receptacle being defined by an interior region of the insert, at least a portion of the second receptacle extending beneath the first receptacle, the insert including an outer surface, the outer surface having an uppermost surface, the uppermost surface substantially enclosing the second receptacle and having an opening in the form of a slot to accept one of the strips at a time, said opening having a width equal to the width of the used elongate strips plus minimal clearance, and said opening having a thickness equal to the thickness of the elongate strips plus minimal clearance, wherein the opening is in communication with the interior region.

2. The assembly of claim 1, wherein the first receptacle comprises two first receptacles, the second receptacle including a first portion extends in a horizontal direction beneath the two first receptacles, the second receptacle also including a second portion that extends upward from a substantially central location along a length of the first portion and between the two first receptacles.

3. The assembly of claim 1, wherein the vial further comprises a cap that removably affixes over the opening to move the vial between an opened position and a closed position, and wherein the cap and vial are configured to engage in a moisture tight seal.

4. The assembly of claim 3, wherein the cap is connected to the vial by a hinge.

5. The assembly of claim 4, wherein the vial comprises a side wall that is tubular and has a generally oval cross-sectional shape.

6. The assembly of claim 1, wherein the vial further includes a desiccant liner.

7. A vial and insert assembly, comprising:
a vial having an interior and an opening leading to the interior; and
an insert configured to fit within the interior, the insert having a first receptacle for housing a plurality of unused elongate strips and a second receptacle for housing a plurality of used elongate strips, said unused and used elongate strips having a length, a width and a thickness, the second receptacle being defined by an interior region of the insert, at least a portion of the second receptacle extending beneath the first receptacle, the insert including an outer surface, the outer surface having an uppermost surface, the uppermost surface substantially enclosing the second receptacle and having an opening in the form of a slot to accept one of the strips at a time, said opening having a width equal to the width of the used elongate strips plus minimal clearance, and said opening having a thickness equal to the thickness of the elongate strips plus minimal clearance, wherein the opening is in communication with the interior region, said interior region of the second receptacle having a vertical height extending from the uppermost surface to a bottom wall of the second receptacle, wherein the vertical height is greater than the length of the used elongate strips.

8. The assembly of claim 7, wherein the first receptacle comprises two first receptacles, the second receptacle including a first portion that extends in a horizontal direction beneath the two first receptacles, the second receptacle also including a second portion that extends upward from a substantially central location along a length of the first portion and between the two first receptacles.

9. The assembly of claim 7, wherein the vial further comprises a cap that removably affixes over the opening to move the vial between an opened position and a closed position, and wherein the cap and vial are configured to engage in a moisture tight seal.

10. The assembly of claim 9, wherein the cap is connected to the vial by a hinge.

11. The assembly of claim 10, wherein the vial comprises a side wall that is tubular and has a generally oval cross-sectional shape.

12. The assembly of claim 7, wherein the vial further includes a desiccant liner.

\* \* \* \* \*